(12) United States Patent
Spears et al.

(10) Patent No.: US 6,607,698 B1
(45) Date of Patent: Aug. 19, 2003

(54) METHOD FOR GENERALIZED EXTRACORPOREAL SUPPORT

(75) Inventors: J. Richard Spears, Bloomfield Hills, MI (US); Seth A. Foerster, San Clemente, CA (US); James M. Gessert, Santa Ana, CA (US); Paul J. Zalesky, Huntington Beach, CA (US)

(73) Assignees: TherOx, Inc., Irvine, CA (US); Wayne State University, Detroit, MI (US)

( * ) Notice: Subject to any disclaimer, the term of this patent is extended or adjusted under 35 U.S.C. 154(b) by 0 days.

(21) Appl. No.: 08/915,532

(22) Filed: Aug. 15, 1997

(51) Int. Cl.[7] .......................... A61M 1/34; A61M 1/36; A61M 37/00

(52) U.S. Cl. .......................... 422/45; 422/44; 604/4.01; 604/6.14; 604/6.16; 261/DIG. 28

(58) Field of Search .......................... 604/4, 131, 4.01, 604/5.01, 6.16, 3.14, 506–508; 128/DIG. 3; 600/16; 261/DIG. 28; 422/44, 45

(56) References Cited

U.S. PATENT DOCUMENTS

| | | | |
|---|---|---|---|
| 2,474,665 A | 6/1949 | Guarino | 128/214 |
| 2,827,901 A | 3/1958 | Jones | 128/214 |
| 2,847,008 A | 8/1958 | Taylor et al. | 128/214 |
| 2,876,769 A | 3/1959 | Cordova | 128/214 |
| 3,142,296 A | 7/1964 | Love | 128/214 |
| 3,437,450 A | 4/1969 | Greenwood | 23/285.5 |
| 3,512,517 A | 5/1970 | Kadish et al. | 128/2 |
| 4,041,180 A | 8/1977 | Wilson | 426/11 |
| 4,317,731 A * | 3/1982 | Roberts, Jr. et al. | 210/741 |
| 4,442,843 A * | 4/1984 | Rasor et al. | 128/660 |
| 4,459,977 A * | 7/1984 | Pizon et al. | 128/1 |
| 4,466,804 A | 8/1984 | Hino | 604/4 |
| 4,493,692 A * | 1/1985 | Reed | 128/DIG. 3 |
| 4,540,399 A | 9/1985 | Litzie et al. | 607/4 |
| 4,596,210 A | 6/1986 | Schmidtke | 123/1 A |

(List continued on next page.)

FOREIGN PATENT DOCUMENTS

| | | | |
|---|---|---|---|
| EP | 0291612 | * 11/1988 | 5/14 |
| WO | WO 92/14404 | 9/1992 | A61B/6/00 |
| WO | WO 92/14976 | 9/1992 | F25B/19/00 |
| WO | WO 95/13843 | 5/1995 | A61B/37/00 |
| WO | WO 96/01593 | 1/1996 | A61B/19/00 |
| WO | WO 96/17565 | 6/1996 | A61F/5/00 |
| WO | WO 96/40334 | 12/1996 | A61M/15/00 |
| WO | WO 96/41987 | 12/1996 | |
| WO | WO 96/19713 | 6/1997 | |
| WO | WO 97/49447 | 12/1997 | A61M/25/00 |
| WO | WO 98/16203 | 4/1998 | A61K/9/133 |
| WO | WO 98/46340 | 10/1998 | |

OTHER PUBLICATIONS

Padmavathy Guttikonda et al., "Effect of Topical O2–Supersaturated Normal Saline on UV Light–Induced Mouse Ear Inflammation," SSID Dermatology Session Abstract, vol. 44, No. 1, p. 51A, Jan. 1996.

John Metschl, "The Supersaturation of Gases in Water and Certain Organic Liquids," vol. 28, pp. 417–437, 1924.

(List continued on next page.)

Primary Examiner—Angela D. Sykes
Assistant Examiner—P M Bianco
(74) Attorney, Agent, or Firm—Margaret A. Kivinski (57) ABSTRACT

A system and method for increasing gas concentration in blood which has use as a generalized extracorporeal system and method to treat hypoxemic blood from a patient by mixing the blood with an oxygen supersaturated solution to generate hyperoxemic blood to be infused back to the patient. The extracorporeal system comprises an extracorporeal tubing through which blood from the patient is circulated, a blood pump for withdrawing blood from and delivering blood to the patient, at least one channel for delivering oxygen-supersaturated fluid and a mixing region for introducing supersaturated fluid without bubble formation. By infusing the oxygen-supersaturated fluid into the hypoxemic or normoxemic blood from the patient, hyperoxemic blood is thereby produced. The hyperoxemic blood is then returned to a central vein, right heart or artery of the patient with the blood pump at approximately the same volume delivery rate as blood volume withdrawal rate.

26 Claims, 4 Drawing Sheets

U.S. PATENT DOCUMENTS

| | | | |
|---|---|---|---|
| 4,648,384 A | | 3/1987 | Schmukler |
| 4,657,756 A | * | 4/1987 | Rasor et al. ................... 424/9 |
| 4,664,680 A | | 5/1987 | Weber ........................... 55/48 |
| 4,681,119 A | * | 7/1987 | Rasor et al. ................ 128/660 |
| 4,769,241 A | | 9/1988 | Heldebrant et al. ......... 424/161 |
| 4,828,543 A | | 5/1989 | Weiss et al. ................... 604/4 |
| 4,871,450 A | | 10/1989 | Goodrich et al. ........... 210/151 |
| 4,874,509 A | | 10/1989 | Bullock ....................... 210/169 |
| 4,919,895 A | | 4/1990 | Heldebrant et al. ......... 422/129 |
| 4,973,558 A | | 11/1990 | Wilson et al. ........ 435/240.242 |
| 5,006,352 A | | 4/1991 | Zelenák née Zoltai et al. ........................... 426/67 |
| 5,084,011 A | * | 1/1992 | Grady ......................... 604/24 |
| 5,086,620 A | | 2/1992 | Spears ....................... 62/51.1 |
| 5,106,363 A | * | 4/1992 | Nobuyoshi .................... 604/4 |
| 5,186,713 A | * | 2/1993 | Raible ........................... 604/4 |
| 5,261,875 A | | 11/1993 | Spears ......................... 604/24 |
| 5,322,500 A | * | 6/1994 | Johnson et al. ................ 604/4 |
| 5,368,555 A | * | 11/1994 | Sussman et al. ............... 604/4 |
| 5,407,424 A | * | 4/1995 | LaFontaine et al. ........... 604/4 |
| 5,407,426 A | * | 4/1995 | Spears ............................. 4/24 |
| 5,466,216 A | * | 11/1995 | Brown et al. .................. 604/33 |
| 5,533,957 A | * | 7/1996 | Aldea .......................... 600/16 |
| 5,569,180 A | * | 10/1996 | Spears ......................... 604/24 |
| 5,599,296 A | * | 2/1997 | Spears ......................... 604/26 |
| 5,612,226 A | * | 3/1997 | Williams .................... 436/167 |
| 5,693,017 A | * | 12/1997 | Spears et al. ............... 604/132 |
| 5,695,717 A | | 12/1997 | Polaschegg et al. .......... 422/48 |
| 5,709,654 A | | 1/1998 | Klatz et al. .................... 604/24 |
| 5,716,318 A | * | 2/1998 | Manning ..................... 600/16 |
| 5,725,492 A | | 3/1998 | Igo et al. ........................ 604/4 |
| 5,730,330 A | | 3/1998 | Reading ..................... 222/113 |
| 5,730,698 A | | 3/1998 | Fischell et al. ................ 600/3 |
| 5,730,935 A | * | 3/1998 | Spears ......................... 422/44 |
| 5,735,934 A | | 4/1998 | Spears ......................... 75/414 |
| 5,752,929 A | | 5/1998 | Klatz et al. .................... 604/51 |
| 5,766,490 A | | 6/1998 | Taylor et al. ............... 210/758 |
| 5,797,874 A | * | 8/1998 | Spears ......................... 604/53 |
| 5,797,876 A | * | 8/1998 | Spears et al. ................. 604/95 |
| 5,814,222 A | | 9/1998 | Zelenák et al. ............. 210/615 |
| 5,817,045 A | * | 10/1998 | Sever, Jr. ........................ 604/4 |
| 5,820,586 A | * | 10/1998 | Booth et al. .................. 604/53 |
| 5,834,519 A | | 11/1998 | Spears ......................... 514/938 |
| 5,843,307 A | | 12/1998 | Faivre et al. ............... 210/192 |
| 5,849,191 A | | 12/1998 | Agranonik et al. ......... 210/608 |
| 5,874,093 A | | 2/1999 | Eliaz et al. .................. 424/401 |
| 5,879,282 A | | 3/1999 | Fischell et al. ................ 600/3 |
| 5,885,467 A | | 3/1999 | Zelenák et al. ............. 210/758 |
| 5,922,305 A | | 7/1999 | Spears ......................... 424/43 |
| 5,957,899 A | | 9/1999 | Spears et al. ............... 604/264 |
| 5,958,377 A | | 9/1999 | Spears ......................... 424/43 |
| 6,180,059 B1 | * | 1/2001 | Divino et al. ................. 422/44 |
| RE37,379 E | * | 9/2001 | Spears ........................ 261/101 |

OTHER PUBLICATIONS

Frank B. Kenrick et al., "Supersaturation of Gases in Liquids," J. Phys. Chem., vol. 28, pp. 1308–1315, 1924.

Robert B. Dean, "The Formation of Bubbles," Journal of Applied Physics, vol. 15, pp. 446–451, May, 1944.

C. Boe et al., "Use of Hyperbaric Oxygen Source in Extracorporeal Oxygenation of Blood," Physiological and Clinical Aspects of Oxygenator Design, Elsevier North–Holland Biomedical Press, Luxembourg, 1976.

Wayne A. Gerth et al., "Gas Supersaturation Thresholds for Spontaneous Cavitation in Water with Gas Equilibration Pressures up to 570 atml," Z. Naturforsch, 31a, pp. 1711–1716, Oct. 5, 1976.

Edvard A. Hemmingsen, "Effect of Surfactants and Electrolytes on the Nucleation of Bubbles in Gas–Supersaturated Solutions," Z. Naturforsch, 33a, pp. 164–171, Oct. 25, 1977.

Yehuda Finkelstein et al., "Formation of Gas Bubbles in Supersaturated Solutions of Gases in Water," A1ChE Journal, vol. 13, No. 9, pp. 1409–1419, Sep., 1985.

Mordecai B. Rubin et al., "Measurements of Critical Supersaturation for Homogeneous Nucleation of Bubbles," American Chemical Society, Dec. 9, 1986.

"Fluosol® 20% Intravascular Perfluorochemical Emulsion Product Information," Alpha Therapeutic Corporation Los Angeles, California, pp. 1–8, Dec. 1989.

J. Richard Spears et al., "Potential Intravascular Oxygenation with Oxygen Clathrate Hydrate," (Abstract 388), Abstracts From the $62^{th}$ Scientific Sessions, Circulation, vol. 80, Suppl. I, pp. I–97, 1992.

Taijiro Sueda et al., "Evaluation of Two New Liquid–Liquid Oxygenators," ASAIO Journal, pp. 923–928, 1993.

J. Richard Spears et al., "Myocardial Protection With a Perfusion Guidewire During Balloon Angioplasty in a Canine Model," (Abstracts/Poster 1032–30), JACC, vol. 27, Suppl. A, p. 392A, Feb. 1996.

J. Richard Spears, "Advances in the Management of Respiratory Failure—Aqueous Preparations of Oxygen," American Society for Artificial Internal Organs, Inc., vol. 42, No. 3, May–Jun., 1996.

J. Richard Spears et al., "Hyperoxemic Perfusion with Aqueous Oxygen Improves LV Function During Experimental MI–Reperfusion," (Abstract 2038), Circulation, vol. 96, Abstracts from the $70^{th}$ Scientific Sessions, Supplement I, pp. I–364–I–365, 1997.

Richard Maas et al., "Superoxygenation Process Treats Highly Concentrated Wastewaters," WATER/Engineering & Management, pp. 29–33, 39, Feb. 1997.

J. R. Spears et al., "Intraaortic Infusion of Oxygen in a Rabbit Model," (Abstracts/Poster 1014–155), JACC, vol. 29, Suppl. A, pp. 317A–318A, Feb. 1997.

Product Monograph, Fluosol® 20% Intravascular Perfluorchemical Emulsion, "Delivers Oxygen to Protect the Heart During PTCA," Alpha Therapeutic Corporation, pp. 3–30.

E. Newton Harvey et al., "Bubble Formation In Animals," J. Cell. Comp. Physiol., vol. 24, pp. 23–34.

Pieter Stroev et al., "Supersaturated fluorocarbon as an oxygen source," Physiological and Clinical Aspects of Oxygenator Design, Elsevier North–Holland Biomedical Press, pp. 129–139, Luxembourg, 1976.

Edvard A. Hemmingsen, "Cavitation in gas–supersaturated solutions," Journal of Applied Physics, vol. 46, No. 1, pp. 213–218, Jan. 1976.

Armand A. Lefemine et al., "Increased oxygen pressure to improve the efficiency of membrane oxygenators," Medical Instrumentation, vol. 10, No. 6, pp. 304–308, Nov.–Dec. 1976.

Brian A. Cason, et al., "Effects of High Arterial Oxygen Tension on Function, Blood Flow Distribution, and Metabolism in Ischemic Myocardium," Circulation, vol. 85, No. 2, pp. 828–838, Feb. 1992.

Adrian H. Shandling et al., "Hyperbaric oxygen and thrombolysis in myocardial infarction: The "HOT MI" Pilot Study," American Heart Journal, vol. 134, No. 3, pp. 544–550, Sep. 1997.

Therapeutic Hyperoxia Diminishes Myocardial Stunning, Brian A. Cason, M.D, et al.

CORFLO Active Perfusion System for Coronary Angioplasty, Leocor, Inc.

Percutaneous Transluminal coronary Angioplasty with Hemoperfusion, R. Snyder, et al.

Reduction of Ischemia With a New Flow–Adjustable Hemoperfusion Pump During Coronary Angioplasty, Germano DiSciascio, M.D., et al.

$22^{nd}$ International Joint Conference on Storke and Cerebral Circulation, Disneyland Hotel, Anaheim, California, Feb. 6–8, 1997.

* cited by examiner

METHOD FOR GENERALIZED EXTRACORPOREAL SUPPORT

FIELD OF THE INVENTION

The present invention generally relates to a generalized extracorporeal support system and method to oxygenate or hyper-oxygenate blood. More specifically, the present invention relates to a generalized extracorporeal support system and method to oxygenate blood from a patient by withdrawing the blood and mixing the blood with an oxygen supersaturated solution for localized or systemic infusion back to the patient.

BACKGROUND OF THE INVENTION

When a patient suffers from acute or transient ischemia, oxygenation and delivery of blood to ischemic and postischemic tissue and/or organ sites is desired in order to prevent or minimize damage to the tissue and/or organ sites. For example, when a patient suffers from an acute myocardial infarction or a heart attack, support of the myocardium during or immediately following the infarction is desired. During a heart attack, the coronary arteries fail to provide adequate blood flow to the heart muscle. If the lack of a supply of oxygenated blood to the heart muscle continues for a prolonged period of time, irreversible damage to the heart can result.

In addition, many patients suffer reperfusion injury, i.e. slow coronary reflow or "no reflow", following successful angioplasty of occlusions responsible for an acute myocardial infarction or myocardial ischemia. To prevent or minimize reperfusion injury, hyperoxemic blood may be actively perfused into the coronary artery to improve blood flow with increased intracoronary pressure. In addition, the high level of oxygenation in the blood should improve oxygen delivery when diffusional distances between capillaries with normal blood flow are large. Finally, the compensatory hypercontractility of the normally perfused left ventricular segments may also benefit from an increase in oxygen supply.

Furthermore, during percutaneous transluminal coronary angioplasty (PTCA), the balloon inflation time is limited by the patient's tolerance to ischemia caused by the balloon inflation. Certain patients are especially at risk of ischemia because of the location or type of lesion, the amount of myocardium at risk, or poor left ventricular function, thereby limiting the performance of effective PTCA. Thus, active perfusion of hyperoxemic blood during PTCA is desired to lessen ischemia and to protect and support the myocardium during balloon inflation and to prolong the tolerated inflation time. Active perfusion of hyperoxemic blood after PTCA may also be desired to accelerate reversal of ischemia and/or recovery of myocardial function.

Conventional membrane or microporous hollow fiber oxygenators have been utilized to oxygenate blood in extracorporeal circuits. In these devices blood is withdrawn from a patient and by circulating the blood through the conventional oxygenator, the blood is oxygenated and delivered back to the patient.

Several disadvantages are associated with use of a conventional oxygenator to directly oxygenate blood. For example, the oxygenator requires a significant priming volume of blood, i.e. the volume of extracorporeal blood within the oxygenator for preparation of oxygen enriched blood. Because more than one quart of priming volume of extracorporeal blood is needed for an adult patient when using the conventional membrane oxygenator, a heat exchanger is usually necessary to maintain the temperature of the blood and a blood transfusion is also frequently necessary. Moreover, due to the large blood membrane oxygenator surface contact area and a relatively slow blood flow rate within the oxygenator, inflammatory cell reactions may be provoked and, in addition, a relatively aggressive anticoagulation therapy such as systemic heparinization may be necessary. Due to the large priming volume of the oxygenator, the oxygenator cannot be easily turned on and off because of the difficulties in flushing the blood from the system with saline and, upon cessation of flow, stagnant blood would result in thrombus formation. Additionally, the large priming volume increases the amount of blood at risk of thrombi formation, especially when stopping and starting the oxygenation. Furthermore, the use of conventional oxygenators to oxygenate blood involves high costs associated with the replacement of the oxygenator for each use. Finally, the maximum partial pressure of oxygen that can be achieved in blood with a conventional oxygenator is 1 bar. As a result of the challenges in using the conventional oxygenators, treatment of regional organ ischemia with conventional oxygenators has not been developed clinically.

With direct intravascular infusion of an oxygen supersaturated physiologic infusate into the blood stream, optimal mixing of the infusate with the blood may be difficult to obtain. For example, inadequate mixing of the infusate with blood may result in dangerous microbubble formation, and direct intravascular infusion would thus require the use of sensors to monitor the intravascular oxygen levels and to detect the intravascular presence of microbubbles.

Accordingly, there remains a need in the art for a safe, simple, efficient and cost-effective system and method for oxygenating a patient's blood by withdrawing and mixing the blood with an oxygen supersaturated physiologic infusate which provides for near physiologic flow rates within the system and which does not require a high priming volume of blood, a heat exchanger or aggressive systemic anticoagulation therapy.

There remains a further need in the art for a system and method for mixing and infusing a patient's blood and oxygen supersaturated physiologic infusate to a tissue or organ site of interest which provides adequate mixing of the infusate with the blood and which provides oxygenation of the blood at a target level.

There remains yet a further need in the art for a system and method for producing and delivering oxygen-supersaturated blood to a tissue or organ site of interest without bubble nucleation or growth during mixing of the infusate with the blood or during infusion in the blood stream.

SUMMARY OF THE INVENTION

The present invention meets the foregoing needs by providing a system and method of treating blood from a patient extracorporeally by mixing the blood with an oxygen supersaturated infusate to generate hyperoxemic blood to be infused back to the patient.

The system of the present invention preferably utilizes aqueous oxygen as the oxygen supersaturated infusate to generate normoxemic or hyperoxemic blood. Aqueous oxygen is a highly concentrated form of oxygen-supersaturated solution that is a liquid phase combination of an aqueous carrier and oxygen, where the volume of dissolved oxygen, normalized to standard temperature and pressure, ranges from approximately 0.5 up to 3 times the volume of the aqueous carrier. Because of the high concentration of oxygen in aqueous oxygen, a relatively small volume of aqueous oxygen can be infused into the blood for alleviation or correction of hypoxemia or production of hyperoxemia. Therefore, the use of aqueous oxygen as the oxygen supersaturated infusate minimizes the volume of the aqueous carrier added to the blood stream.

The system of the present invention provides an extracorporeal tubing, through which blood from a patient is circulated, a blood pump for withdrawing blood from and delivering blood to the patient, an aqueous oxygen generator or pump with output tubes and a chamber for connecting the extracorporeal tubing and the aqueous oxygen output tubes and providing the necessary mixing function. The system may also include sensors for monitoring certain parameters of the blood, access ports for intermittent analysis of the blood, hydraulic components to manage the hydrodynamics of the blood flow, bubble traps and bubble detectors to ensure bubble-free delivery of the oxygenated blood, system shunts or system shutdown devices to manage system related failures and a hemofilter for filtering the aqueous carrier from the hyperoxemic blood prior to infusion of the blood to the patient.

The system and method of the present invention obviates the need for a heat exchanger and for an aggressive, systemic anticoagulation therapy due to the small blood priming volume and the near physiologic blood flow rates through the system. Furthermore, the system and method of the present invention provides adequate mixing and infusion of the aqueous oxygen infusate and the blood without bubble nucleation or growth. The aqueous oxygen infusate can yield a blood $pO_2$ of greater than 1000 mm Hg so as to provide support and expedite the treatment of ischemia with hyperoxemic blood perfusion.

The system and method of the present invention provides for simple blood withdrawal and delivery access via devices already in place in the patient for interventions, such as the side-arm of a sheath and a coronary guide catheter for intracoronary infusion. In addition, easy access to the blood in the extracorporeal system allows for utilization of devices to monitor parameters of the blood in the system and to vary system operations accordingly.

DETAILED DESCRIPTION OF THE INVENTION

The structure and function of the preferred embodiments can best be understood by reference to the drawings. Where the same reference numerals appear in multiple figures, the numerals refer to the same or corresponding structure in those figures.

Figure 1:
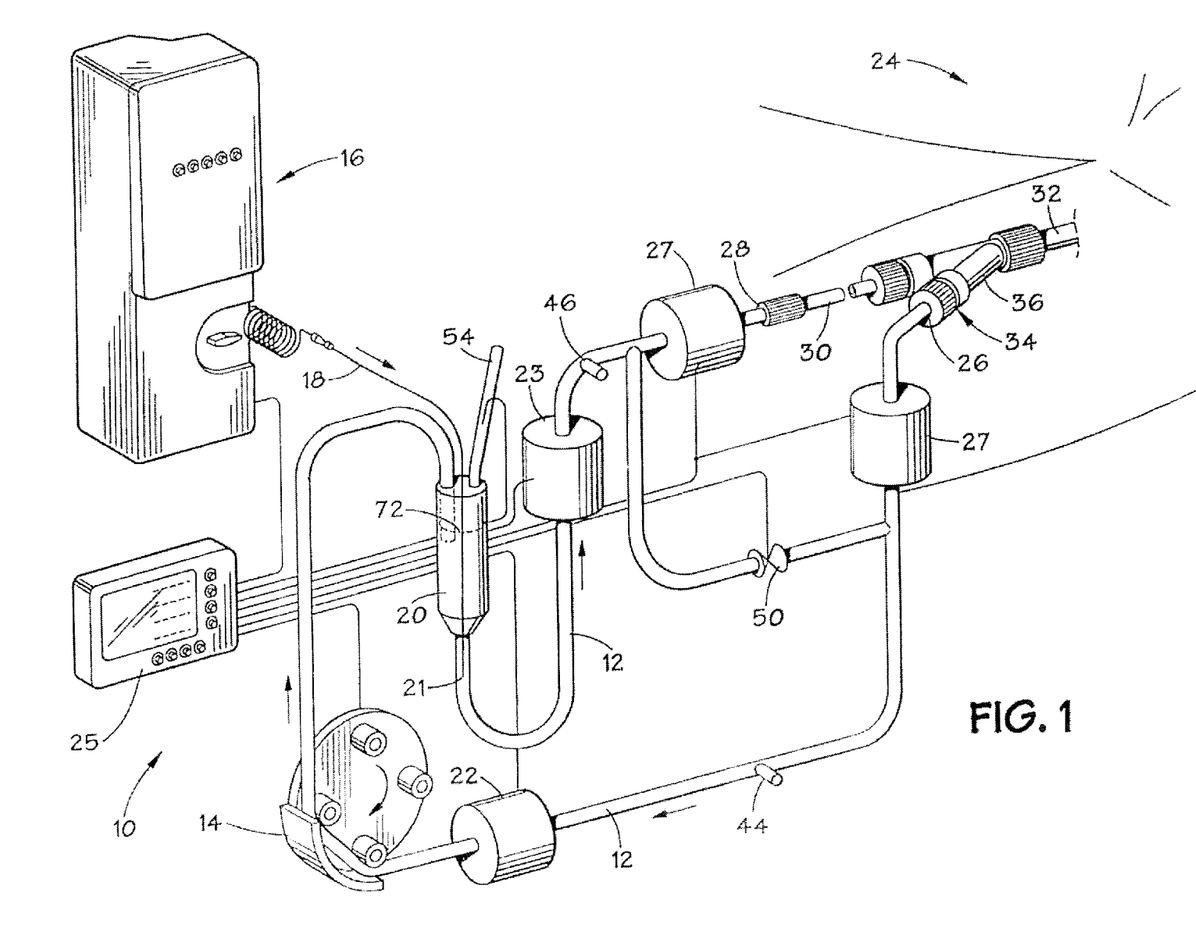
FIG. 1 shows a generalized extracorporeal support system according to an embodiment of the present invention.
Figure 2:
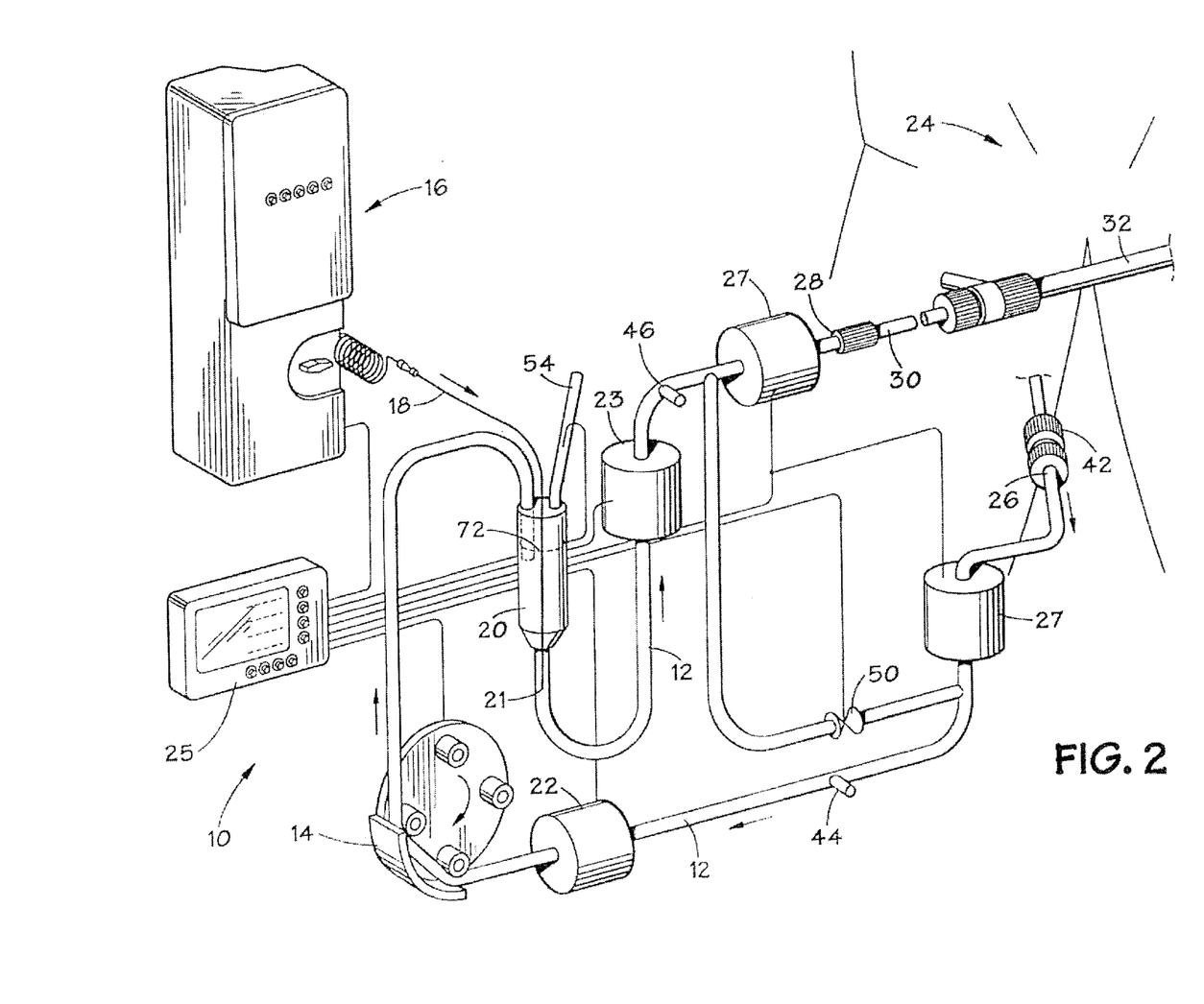
FIG. 2 shows a generalized extracorporeal support system according to an alternative embodiment of the present invention.

As shown in FIGS. 1–2, extracorporeal system 10 comprises extracorporeal tubing 12, through which blood from patient 24 is circulated, blood pump 14 for withdrawing blood from and delivering blood to patient 24, aqueous oxygen generator or pump 16 with output channels 18 and chamber 20 for connecting tubing 12 to channels 18 for introducing aqueous oxygen into the blood.

Blood is withdrawn from patient 24 at a predetermined rate between approximately 25–8000 ml/min into extracorporeal tubing 12 with blood pump 14, such as a roller pump. Aqueous oxygen is generated or loaded into aqueous oxygen generator or pump 16 and introduced to and mixed with the blood within extracorporeal tubing 12. Either normoxemic blood ($pO_2$ of approximately 90–150 mm Hg) or hyperoxemic blood ($pO_2$ of greater than approximately 150 mm Hg) is then returned to patient 24, for example via a central vein, right heart or artery with blood pump 14 at approximately the same volume delivery rate as blood volume withdrawal rate. Each component of extracorporeal system 10 will now be described in detail.

Extracorporeal tubing 12 has input end 26 where hypoxemic or normoxemic blood from patient 24 enters into extracorporeal system 10 and output end 28 where hyperoxemic blood exits from extracorporeal system 10. Output end 28 of extracorporeal tubing 12 is connected to intravascular catheter 30, for example, a conventional coronary angioplasty guide catheter, preferably 6 to 8 French (2.0 to 2.7 mm) in size, or a diagnostic angiographic catheter, preferably 5 to 7 French (1.7 to 2.3 mm) in size. Other suitable delivery devices may be selected by the physician. Intravascular catheter 30 may be inserted and advanced into an artery or vein, depending on the particular application, via introducer or sheath 32, preferably approximately 8.5 French (2.8 mm) in size. Again other suitable introducers may be selected.

As shown in FIG. 1, input end 26 of tubing 12 may be connected to sheath 32 via side arm 36 of Y-connector 34 for withdrawing blood from patient 24. Blood may be withdrawn from patient 24 via an annular opening (not shown) defined around catheter 30 by sheath 32. Sheath 32 is preferably approximately 8.0 French (2.7 mm) or 8.5 French (2.8 mm) in size. If blood flow into tubing 12 is inadequate because of a tight fit between catheter 30 and sheath 32, a larger sheath 32 may be used. Alternatively, as shown in FIG. 2, blood withdrawal may occur via a separate sheath 42 inserted and advanced into another artery or vein of patient 24, such as the contralateral femoral artery. Such a separate withdrawal sheath may be preferably approximately 6 French (2 mm) in size.

Blood pump 14 facilitates blood withdrawal from patient 24 into tubing 12 at a predetermined blood flow rate of between approximately 25–8000 ml/min. At blood flow rates of greater than 500 ml/min, a larger catheter for blood withdrawal and delivery may be required. For regional organ perfusion and neonatal lung support, a preferred blood flow rate is between approximately 50–300 ml/min. Preferably, tubing 12 is a clinically approved, heparin-bonded PVC or polyurethane tubing. By way of example, tubing 12 is approximately 2 meters in length with an inner diameter of approximately 3 mm. Thus, tubing 12 requires a priming volume of approximately 15 ml. Because of the relatively low priming volume for extracorporeal system 10, the need for a heat exchanger and a blood transfusion is obviated. In addition, the relatively small blood-to-tubing contact area of approximately 0.02 $m^2$ reduces the need for systemic anticoagulation within extracorporeal system 10 and may minimize blood-material inflammatory cell interactions. Extracorporeal system 10 is further resistant to thrombus formation because the blood flow velocity in tubing 12 is near physiologic flow velocities.

Blood pump 14 is preferably a clinically approved roller pump, although other pumps such as a centrifugal pump may also be used. Roller pump 14 is preferred as it provides an inexpensive, atraumatic, non-blood contact method of pumping the blood.

The upper end of chamber 20 receives and accumulates blood from tubing 12. The lower end of chamber 20 delivers blood at a steady flow rate to mixing region 39 where the aqueous oxygen is introduced via channels 18. To ensure that chamber 20 contains a proper volume of blood, preferably approximately 5 cc in an exemplary embodiment, chamber 20 provides blood level indicator 72 and port 54 to allow the injection and removal of air in order to adjust the volume of blood contained in chamber 20. The volume of compressed air in the upper portion of chamber 20 is preferably approximately 3 cc. Thus, with a priming volume of approximately 15 cc for tubing 12 and approximately 5 cc for chamber 20, the total priming volume for system 10 is only approximately 20 cc.

By utilizing a volume of compressed air, chamber 20 may also ensure the smooth flow of blood in tubing 12, particularly downstream of chamber 20. A smooth flow of blood in tubing 12 is preferred to match the smooth flow of the aqueous oxygen from pump 16 in order to maximize the $pO_2$ level (especially at $pO_2$'s above 400 mm) which the blood can carry. For example, where blood pump 14 is a roller pump, a zero pressure phase occurs when each roller is rotated away from tubing 12 during the pump's rotation. Thus, chamber 20 can utilize the volume of compressed air to pump the blood through tubing 12 during the zero pressure phases in order to ensure the smooth and constant flow of blood through tubing 12.

Chamber 20 may also function as a bubble trap. Because blood enters at the upper end of chamber 20 and exits from the lower end of chamber 20, any bubbles in the blood would remain in the volume of compressed air at the upper end of chamber 20 and would thereby be removed from the blood.

As previously discussed, extracorporeal system 10 of the present invention preferably utilizes aqueous oxygen as the oxygen supersaturated infusate to generate hyperoxemic blood. Because of the high concentration of oxygen in aqueous oxygen, the volume of aqueous oxygen, and thus the volume of aqueous carrier, infused into the blood stream for alleviation or correction of hypoxemia or production of hyperoxemia is therefore minimized. Aqueous oxygen offers the additional benefit of infusion into hypoxemic or normoxemic liquids under ambient pressure without microbubble nucleation. Thus, aqueous oxygen is the preferred oxygen-supersaturated infusate for generating hyperoxemic blood, although other forms of oxygen-supersaturated infusates with lower oxygen concentrations may also be utilized.

Aqueous oxygen is delivered by aqueous oxygen generator or pump 16 and introduced into the blood in tubing 12 downstream of blood pump 14 via at least one channel 18. Channel 18 preferably includes a plurality of capillary-like lumens which deliver the oxygen-supersaturated fluid while preventing bubble formation. The apparatus and method for preparing oxygen supersaturated fluid disclosed in U.S. Pat. No. 5,407,426, "Method and Apparatus for Delivering Oxygen into Blood", to Spears, incorporated herein by reference, may be utilized to prepare the aqueous oxygen infusate. Other apparatuses and methods such as those disclosed in U.S. Pat. No. 5,569,180, "Method for Delivering a Gas-Supersaturated Fluid to a Gas-Depleted Site and Use Thereof", to Spears and U.S. Pat. No. 5,599,296, "Apparatus and Method of Delivery of Gas-Supersaturated Liquids", to Spears, incorporated herein by reference, may also be used to prepare the aqueous oxygen infusate.

By way of example, aqueous oxygen generator 16 comprises a housing containing a high pressure pump and sensors for monitoring pressure, temperature, and flow rate of the aqueous oxygen. The high pressure pump contains a physiologic solution, such as normal saline, as the aqueous carrier. The aqueous carrier is equilibrated with oxygen at partial pressures of approximately 1.5–13 MPa (218–1,885 psi), corresponding to an oxygen concentration of between approximately 0.5–3 ml $O_2$/ml aqueous carrier, approximately 2.5 to 15 times the oxygen carrying capacity of blood. More preferably, the aqueous carrier is equilibrated with oxygen at partial pressures of approximately 3.4–6.9 MPa (500–1,000 psi), corresponding to an oxygen concentration of between approximately 1–2 ml $O_2$/ml aqueous carrier.

The aqueous oxygen in aqueous oxygen generator 16 is then hydrostatically compressed to approximately 6.9–100 MPa (1,000–14,500 psi), and more preferably approximately 6.9–69 MPa (1,000–10,000 psi) for one minute or more to dissolve and remove any remaining gas nuclei in aqueous oxygen generator 16. A similar application of hydrostatic pressure within the lumens of output channels 18 removes surface nuclei therein.

Aqueous oxygen generator or pump 16 then delivers aqueous oxygen through output channels 18 into the blood in tubing 12 without microbubble nucleation. Output channels 18 are preferably an array of fused capillary channels made of glass, silica, ceramic, metal, polymeric or any other suitable materials. A sterile fluid pathway is maintained throughout aqueous oxygen generator or pump 16 and a 0.2 $\mu$m filter may be provided proximal to output channels 18, distal to aqueous oxygen generator or pump 16 for further assurance of sterility. Ends of output channels 18 distal to aqueous oxygen generator or pump 16 are sealingly connected into tubing 12.

Because the maximum infusion flow velocity of the aqueous oxygen effluent relative to the velocity of blood in tubing 12 is approximately 4 m/sec before the onset of mechanical damage to erythrocytes, flow velocity of the aqueous oxygen effluent relative to the velocity of blood in tubing 12 through each capillary channel 18 is 4 m/sec or less.

Figure 3:
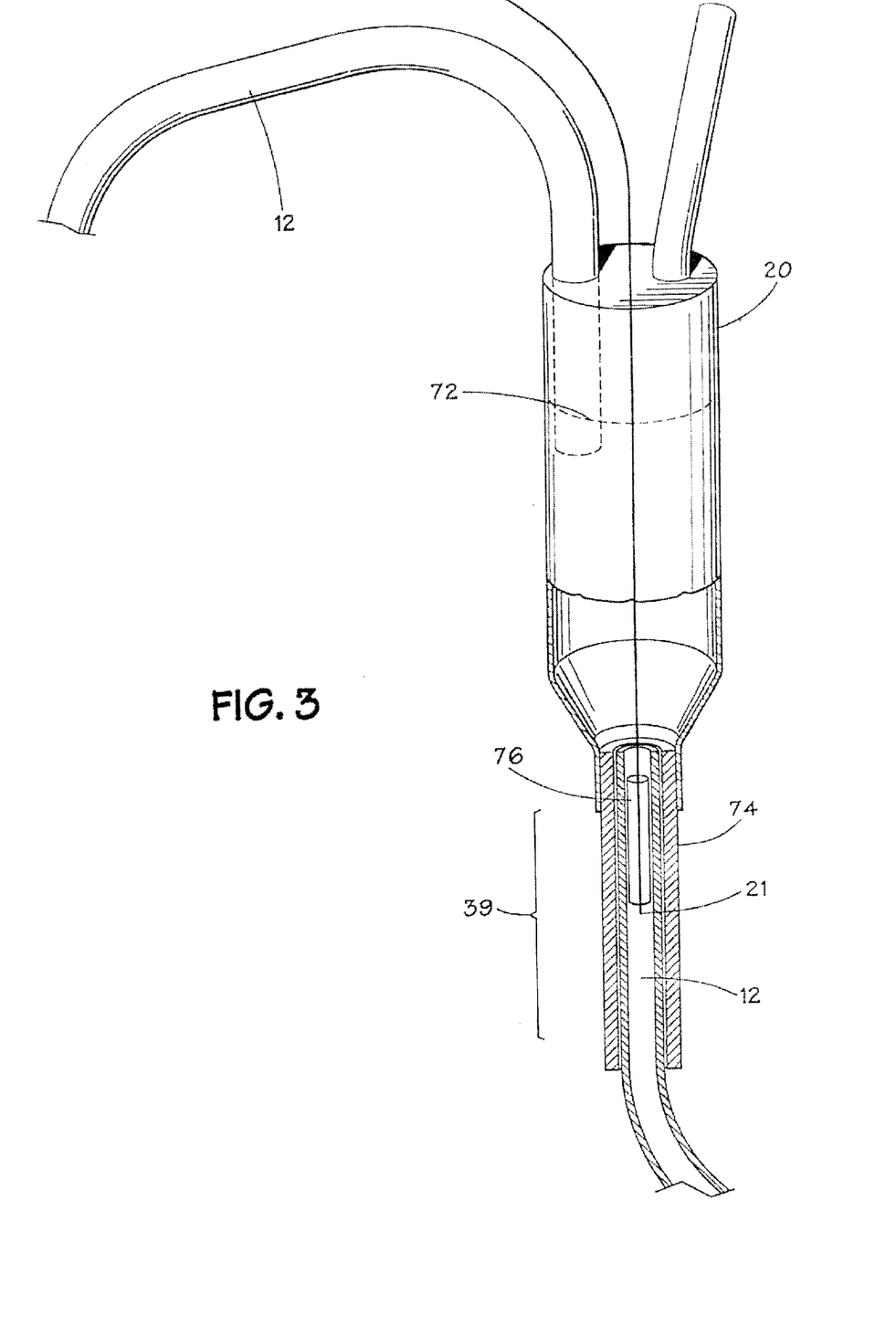
FIG. 3 is a partial cross-sectional view of a entering fin, a chamber and mixing region for aqueous oxygen introduction in the system of FIGS. 1 and 2.

Stable aqueous oxygen injection is achieved according to the embodiment of FIG. 3 by minimizing the difference in the flow velocity of the blood and the aqueous oxygen at injection site 21. Because the exit velocity of the aqueous oxygen at site 21 is relatively faster than the blood flow velocity in tubing 12, site 21 is preferably located at the center of tubing 12 where the blood flow velocity is highest. Thus, ends of output channels 18 may be connected to centering fin 76 to ensure that the injection of aqueous oxygen is at or near the center of tubing 12.

In order to control the blood velocity profile in tubing 12 to ensure the highest velocity at the center of the tubing 12 or at injection site 21, straightening tube 74 is connected to tubing 12 in mixing region 39. Alternatively, a piece of integral stiff tubing may be used. A length of 10 to 30 times the inner diameter of tubing 12 is preferred to ensure complete development of laminar flow of the blood prior to injection site 21. Straightening tube 74 also reduces the possibility that the high velocity aqueous oxygen injected at site 21 cross laminar flow lines to slower flowing blood by aligning straightening fin 76 and output channels 18 axially with the laminar flow.

Straightening tube 74 also helps to prevent direct contact between tubing 12 and high velocity aqueous oxygen. Such direct contact between tubing 12 and high velocity aqueous oxygen may cause bubble nucleation. To further prevent such direct contact, tubing 12 may be coated with blood proteins by perfusing blood through tubing 12 for at least several minutes before initiating infusion of aqueous oxygen.

Mixing of the aqueous oxygen with the blood in tubing 12 results from a combination mass diffusion across laminar flow lines and convective transfer over a length of approximately 1 meter of tubing 12 downstream of injection site 21.

The embodiment shown in FIG. 3 for aqueous oxygen introduction maximizes the amount of oxygen that may be infused into the blood given constraints of output channel 18 size and tubing 12 size. However, in clinical practice there may be concerns which override the priority to maximize the $pO_2$ performance of the system. The alternative embodiment shown in FIG. 4 is designed to reduce the concern of triggering inflammatory cell reactions by system components, while being capable of infusing desired amounts of aqueous oxygen.

Figure 4:
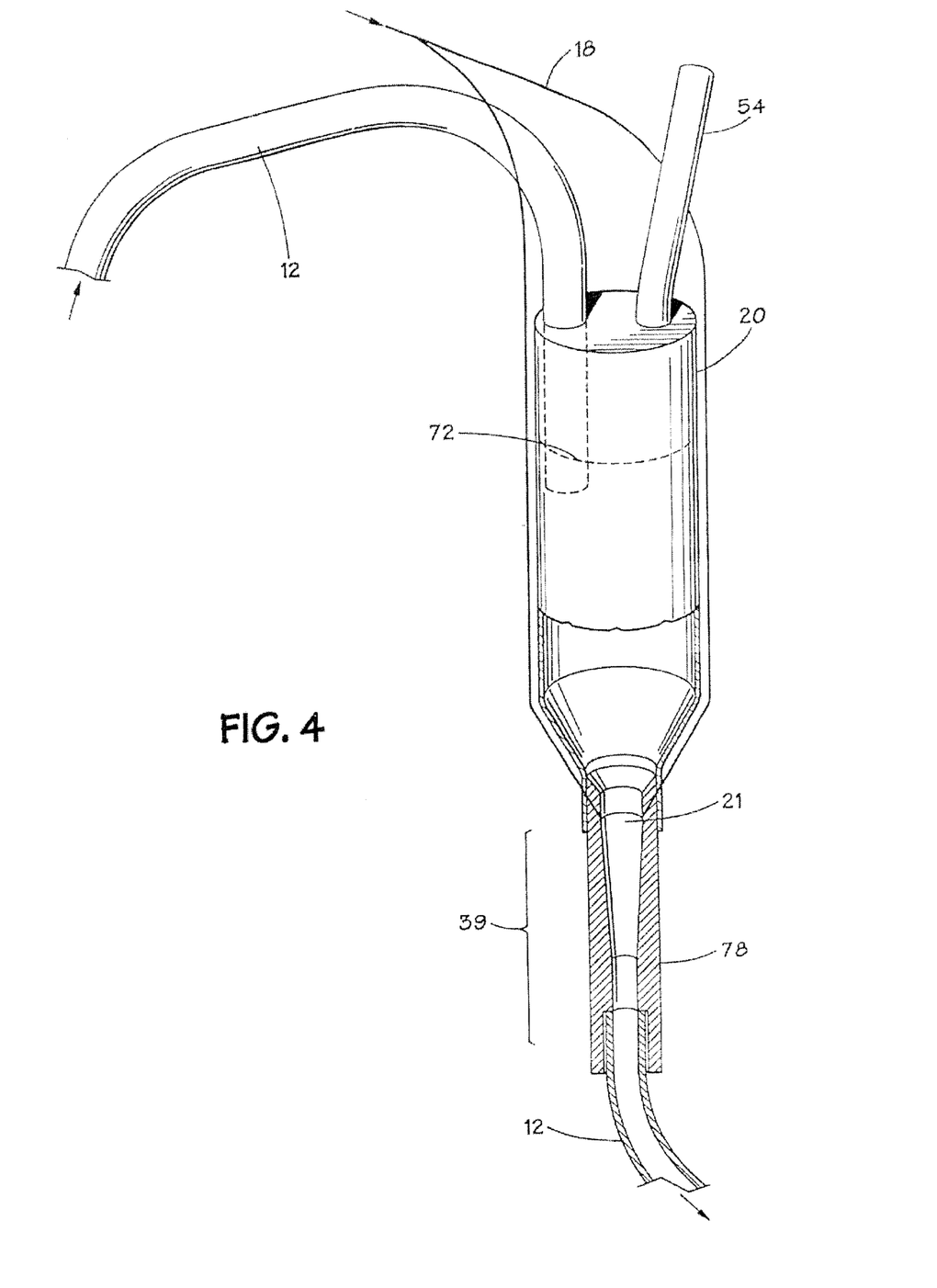
FIG. 4 is a partial cross-sectional view of an alternative embodiment of the chamber and mixing region for aqueous oxygen introduction.

Inflammatory cell reactions may be reduced, as shown in FIG. 4, by minimizing the blood contact surface area especially in the high velocity areas of the velocity profile in mixing region 39. The output channels 18 have been taken out of the central blood flow as has the centering fin 76. The output channels are instead positioned in a slower part of the blood flow along the tube wall by means of infusion chamber 78. Infusion chamber 78 preferably holds output channels 18 at approximately 45° with respect to ease the introduction of the aqueous oxygen into the blood flow. The 45° angle also increases the path length to the opposite wall of the chamber to minimize the blood flow propensity of contact with the opposing wall.

As illustrated infusion chamber 78 preferably has a larger diameter at the site of injection to slow blood flow velocity. This minimizes the turbulent fluid interaction caused by injecting aqueous oxygen across laminar flow boundaries. The varying diameter in the mixing region may also be employed with the embodiment of FIG. 3 to further control mixing conditions.

More output flow channels may be utilized in this embodiment (as compared to FIG. 3) due to the relative velocity constraint imposed by the maximum tolerable shear force of blood before inflammatory cell reactions start to occur. This means that typically a given output channel 18 in the FIG. 4 embodiment may deliver less aqueous oxygen which may therefore require a greater number of channels to achieve a desired total flow.

In each of the embodiments shown in FIGS. 3 and 4, the flow in mixing region 39 is controlled in order to reduce or eliminate turbulence which might otherwise result from mixing two fluids having disparate properties and velocities in order to achieve a homogeneous mixture. Excessive turbulence is believed to be undesirable as it may promote bubble formation and damage fragile cells. A person of ordinary skill in the art may apply the teachings of the present invention to develop other suitable means for introducing the gas infusate without departing from the scope of the invention.

Extracorporeal system 10 preferably provides one or more monitoring devices 22, 23 in communication with the blood in tubing 12 for monitoring one or more parameters of the hypoxemic or normoxemic blood and the hyperoxemic blood, respectively. Monitoring devices 22 for monitoring the hypoxemic or normoxemic blood from patient 24 in tubing 12 are disposed between input end 26 of tubing 12 and connector 20. Similarly, monitoring devices 23 for monitoring hyperoxemic blood in tubing 12 are disposed between connector 20 and output end 28 of tubing 12.

Monitoring devices 22, 23 preferably comprise oxygen level sensors for continuous monitoring of the oxygen saturation level or the $pO_2$ level of both the hypoxemic or normoxemic blood and the hyperoxemic blood in tubing 12 for control of the level of oxygenation. A commercially available device may be used to continuously monitor the oxygen levels of blood in tubing 12. For example, the oxygen level sensor may be a $pO_2$ electrode sensor or a device to detect the oxygen saturation level in blood by transmission or reflectance oximetry. Monitoring devices 22, 23 may also comprise a flow meter to monitor the flow rate of the blood. In a preferred embodiment, an upstream sensor monitors the oxyhemoglobin saturation level and a downstream sensor monitors oxygen partial pressure.

Monitoring devices 22 and 23 may further comprise pressure sensors. A pressure sensor may additionally or alternatively be located at port 54. If the blood pressure is not within predetermined limits, controller 25 may activate system shut-down actuators 27 to discontinue circulation of blood to and from patient 24 until the blood pressure is within the predetermined limits. When activators 27 are activated, controller 25 also terminates delivery of aqueous oxygen through output channels 18 and opens loop shunt 50 in order to recirculate blood in tubing 12 via loop shunt 50. Loop shunt 50 may also be employed to recirculate blood through tubing 12 in order to trap bubbles in chamber 20.

Extracorporeal system 10 preferably further provides one or more access ports 44, 46 to permit infusion of drugs and/or nutrients as desired and to permit withdrawal of blood samples for intermittent analysis of the hypoxemic or normoxemic and hyperoxemic blood, respectively. Access port 44 for access to the hypoxemic or normoxemic blood from patient 24 in tubing 12 is disposed between input end 26 of tubing 12 and connector 20. Similarly, access port 46 for access to the hyperoxemic blood in tubing 12 is disposed between connector 20 and output end 28 of tubing 12.

Due to the relatively simple components of extracorporeal system 10, setup and connection of extracorporeal system 10 to patient 24 is simple and quick. The simpler circuit also allows nurses to monitor the functions of extracorporeal system 10 after the initial setup. In addition, because only tubing 12 and output channels 18 come into contact with the patient's blood and thus are disposed of after each use, use of extracorporeal system 10 is very cost effective.

Extracorporeal system 10 provides various controls for controlling parameters such as the blood withdrawal and delivery rate and the pressure and flow rate of the aqueous oxygen, at least in part in response to the output of monitoring devices 22, 23. The ratio of aqueous oxygen flow to blood flow can also be adjusted according to the output of monitoring devices 22, 23 to provide an optimal or target level of blood oxygenation. Provision is made for access port and attachment to enable continuous or intermittent drip of Heparin or equivalent anticoagulant to physician-specified level of systemic heparinization. This provision minimizes the potential for extracorporeal circuit formation or shedding of thrombus.

Control of pressure and flow rate of aqueous oxygen into tubing 12 at connector 20 is provided by controller 25. By controlling the pressure and flow rate of aqueous oxygen into tubing 12, the target $pO_2$ in the hyperoxemic blood in tubing 12 and the target $pO_2$ in the blood stream of patient 24 can thereby be achieved. In addition, in response to detection of microbubbles in tubing 12, controller 25 may automatically terminate the flow of aqueous oxygen from aqueous oxygen pump 16, adjust blood pump 14 to vary the blood flow rate and/or adjust aqueous oxygen pump 16 to vary the aqueous oxygen delivery. Detection of microbubbles in tubing 12 may be achieved by, for example, the $pO_2$ of the hyperoxemic blood not registering as predicted in $pO_2$ sensor 22 according to the known parameters such as the aqueous oxygen flow rate, the oxygen concentration of the aqueous oxygen and the $pO_2$ of the normoxemic or hypoxemic blood in tubing 12.

To further prevent thrombus formation and/or bubble nucleation (small thrombi may contribute to bubble formation by providing small nuclei on which bubbles form), the inner surfaces of tubing 12 and/or output channels 18 may be pre-wetted with a liquid, such as water, ethanol, or a heparin solution. Priming the fluid contact surface with such liquids facilitates the elimination of surface bubble nuclei. They also facilitate the prevention of bubble nucleation by pre-wetting a fluid contact surface so that when a fluid with high oxygen concentrations first contact such a pre-wetted surface, the fluid contacts a smooth pre-wetted surface rather than a dry surface which more readily promotes bubble nucleation in the fluid. As noted before, perfusion of blood without an aqueous oxygen infusate provides a protein surface coating the fluid contacting surface and facilitating inhibition of bubble nucleation on the surface.

Applications of extracorporeal system 10 will now be described. Extracorporeal system 10 may be utilized intra-arterially for regional support of ischemic and postischemic organs or tissues or as an extracorporeal bypass for lung support and improvement in the systemic oxygenation.

For coronary arterial delivery of hyperoxemic blood from extracorporeal system 10, an end of intravascular catheter 30 distal to extracorporeal system 10 is preferably anchored in or proximal to a major branch of the coronary artery, for example, in the ostium of the left coronary artery. Additionally, a hollow guidewire positioned through intravascular catheter 30 may be provided for additional catheter placement stability. The guidewire may be a conventional angioplasty guidewire, preferably with an outer diameter in the approximate range of 0.010"–0.018" and more preferably in the approximate range of 0.014"–0.016".

More preferably, a hollow guidewire is provided that has an inner diameter in the approximate range of 0.008"–0.015" and more preferably in the approximate range of 0.009"–0.011". Furthermore, the hollow guidewire for anchoring catheter 30 is preferably a perfusion guidewire with a porous velocity diffuser to allow a saline flush solution under a pressure greater than the systolic arterial pressure, such as in a standard pressure intravenous bag, to slowly "weep" or flush out along most of the intracoronary length of the guidewire at a rate of approximately 2–5 ml/hr. Because the flushing of the solution from the velocity diffuser facilitates keeping blood elements away from the surface of the guidewire, the guidewire is inherently self-cleaning and therefore resistant to thrombus formation even during a prolonged period of time. As used herein, intravascular catheter refers to any device which may be advanced through the patient's vasculature to a desired region for fluid delivery.

To further inhibit thrombus formation, an anticoagulant can be added to the flush solution. The rate of infusion of the heparinized flush solution is such that the rate of infusion of the anticoagulant or heparin is in the range of 1–10 U/hr to minimize or prevent systemic effects from the anticoagulant. Alternatively, if the patient requires systemic anticoagulation, a high concentration of heparin can be administered at a low volume delivery rate of the flush solution of less than 10 ml/hr. To yet further inhibit thrombus formation, the guidewire may be provided with a heparin coating.

The infusion guidewire can also be used to monitor intracoronary pressure either continuously or intermittently. Preferably, the guidewire alternates between intermittent flushing of the saline flush solution and semi-continuous monitoring of the intracoronary pressure. For example, the guidewire would monitor the intracoronary pressure approximately 99% of the time and flush intermittently during the remaining 1% of the time.

By monitoring the intracoronary pressure, excess infusion of hyperoxemic blood can be prevented. When there is an excessive increase in mean intracoronary pressure, for example, approximately 50 mm Hg increase to approximately 150 mm Hg intracoronary pressure, excess infusion of hyperoxemic blood can be prevented by immediate termination of hyperoxemic blood infusion by extracorporeal system 10.

Monitoring the intracoronary pressure by the guidewire would also facilitate detection of intravascular catheter 30 slipping out of the coronary ostium, for example by a lack of increase in the intracoronary artery pressure despite the blood infusion from extracorporeal system 10.

Alternatively, a Doppler flow wire, such as one manufactured by Cardiometrics, Inc., may also be utilized to ultrasonically monitor the blood flow velocity to prevent excess infusion of hyperoxemic blood. Monitoring the intracoronary blood flow rate by the Doppler flow wire would also facilitate detection of intravascular catheter 30 slipping out of the coronary ostium, for example by a lack of increase in the intracoronary artery flow despite the blood infusion from extracorporeal system 10.

For arterial applications targeting regional support, extracorporeal system 10 can be tailored to support many separate organ and tissue sites, for example the myocardium, the brain (via the cartoid artery) and the central nervous system by appropriate placement of the delivery devices such as intravascular catheter 30. To provide support to tissue or organ sites during acute or transient ischemia, extracorporeal system 10 preferably infuses hyperoxemic blood with $pO_2$ levels of between approximately 200–3000 mm Hg and more preferably 500–1500 mm Hg, compared to the $pO_2$ of normal arterial blood of approximately 100 mm Hg. Preferably, the ratio of infusate to blood flow is in the approximate range of 0.01 to 0.06. Where aqueous oxygen with a concentration in the approximate range of 0.5 to 3.0 ml $O_2$/ml aqueous carrier is utilized, a relatively small volume of aqueous oxygen, in the approximate range of 0.5–6 ml aqueous oxygen per 100 ml of arterial blood flow, is required to be added to the cardiovascular system to achieve hyperoxemic levels in the arterial blood and thereby achieve hours of support without adding excessive volumes of the aqueous carrier into the blood stream. The delivery blood flow rate is in the approximate range of 25–300 ml/min through intravascular catheter 30, corresponding to a rate of aqueous oxygen infusion in the approximate range of 0.25–18 ml/min.

For total or near-total cardiovascular support of patient 24 using extracorporeal system 10 for an arterial-venous or a veno-venous bypass, the rate of hyperoxemic blood infusion can approach the cardiac output blood flow rate which ranges from approximately 5–8 l/min. With an arterial-venous extracorporeal bypass, blood is withdrawn from a great vein or the right atrium and delivered to the aorta. The advantages of the blood infusion rate nearing the cardiac output blood flow rate are that no significant further dilution of the hyperoxemic blood occurs during infusion into the blood stream, so that the final intraarterial $pO_2$ is controlled primarily by the relative rates of blood and aqueous oxygen infusion. In addition, increased blood flow can be provided to tissues with inadequate cardiac arterial blood flow.

Extracorporeal system 10 may be utilized on a regional basis to support the myocardium for periods of hours following an insult such as an acute myocardial infarction or post-therapy myocardial stunning. Extracorporeal system 10 may also be used to treat patients with an acute myocardial infarction who are hemodynamically compromised despite successful angioplasty of the infarct-related coronary artery. After removal of the angioplasty balloon catheter, hyperoxemic arterial blood from extracorporeal system 10 may be infused into the coronary artery at physiologic flow rates of approximately 100 ml/min per major coronary artery branch through intravascular catheter 30.

Hyperoxemic blood can also be infused into the left coronary artery during angioplasty of one of the branches. Such infusion would be expected to improve oxygen delivery to the non-angioplasty part of the heart that is hypercontractile during occlusion of the angioplasty branch. In addition, such perfusion would improve collateral flow and oxygen delivery to the part of the heart directly affected by the angioplasty.

Many patients also suffer from reperfusion injury, i.e. slow coronary reflow or "no reflow", following successful angioplasty of occlusions responsible for an acute myocardial infarction. Utilization of extracorporeal system 10 to actively perfuse hyperoxemic blood into the coronary artery may provide additional benefits to the myocardium by improving flow and increasing the intracoronary pressure. A high $pO_2$ would improve capillary flow by inhibiting adhesion of leukocytes and platelets to vascular endothelium. In addition, the high $pO_2$ of hyperoxemic blood may also improve oxygen delivery when diffusional distances between capillaries with normal blood flow are large. Finally, the compensatory hypercontractility of the normally perfused left ventricular segments may also benefit from an increase in oxygen supply.

For patients who are hypotensive from left ventricular failure, utilization of extracorporeal system 10 for perfusion of hyperoxemic blood may result in acute hemodynamic improvement. Improved perfusion pressure and a higher rate of oxygen delivery may improve hemodynamics in a manner similar to that associated with diastolic augmentation from an intraaortic balloon pump, but the increase in perfusion pressure would occur for the entire cardiac cycle.

As previously discussed, extracorporeal system 10 may also be utilized as a veno-venous or an arterial-venous extracorporeal bypass for lung support and improvement in the systemic oxygenation. To provide systemic support, the oxygen concentration of the aqueous oxygen is approximately 1–3 ml $O_2$/ml aqueous carrier, and more preferably 1–2 ml $O_2$/ml aqueous carrier, which produce $pO_2$ levels in the blood of 70–90 mm Hg, as compared to the $pO_2$ of normal venous blood of approximately 40 mm Hg. Preferably, the ratio of infusate to blood flow is in the approximate range of 0.03 to 0.06. Because of aqueous oxygen's high oxygen concentration, a relatively small volume of aqueous oxygen in the approximate range of 0.5–2 ml/kg/min is required.

For venous applications, catheter 30 is preferably a double lumen catheter with an outer lumen for withdrawing blood from patient 24 and an inner lumen for infusing blood into the patient's blood stream, such as one utilized for standard conventional veno-venous bypass procedures. The outer lumen has multiple side entry ports or holes along the outer shaft of catheter 30 to distribute the negative pressure created by the withdrawal of blood, and thus facilitate blood withdrawal at a high rate without collapsing adjacent veins and without adjacent soft tissue structures blocking the entry ports. The inner lumen of catheter 30 for blood delivery has a sufficiently small inner diameter such that the $pO_2$ of the oxygenated blood is lower than the hydrostatic pressure in the catheter to prevent bubble nucleation during infusion into the patient's blood stream. The relatively small size of the inner lumen additionally confers a relatively high flow velocity of the oxygenated blood, in the approximate range of 30–300 cm/sec, during intravascular infusion and thereby facilitates mixing of the hyperoxemic blood with the blood stream.

During a veno-venous infusion, the oxygenated blood is rapidly mixed with intravascular or intracardiac venous blood. To achieve normoxemia in severely hypoxemic venous blood requires the rate of oxygenated blood infusion to be preferably in the approximate range of 0.25–0.5 and more preferably 0.33–0.5 of the cardiac output blood flow rate, as higher withdrawal rates may collapse the veins.

When extracorporeal system 10 provides support for systemic oxygenation via infusion of aqueous oxygen, for hyperoxemic blood infusion longer than approximately 30 minutes at an infusion rate in the approximate range of 0.5–2 ml/kg/min, the need may arise for a hemofilter to filter out the aqueous carrier in order to prevent excess addition of the aqueous carrier into the cardiovascular system. Thus, for a veno-venous application, extracorporeal system 10 preferably further provides a hemofilter located along tubing 12 between chamber 20 and output end 28 of tubing 12 to remove the excess aqueous carrier from the hyperoxemic blood. As illustrated in FIGS. 1 and 2, the hemofilter is incorporated with monitoring device 23. Alternatively, the filter may be separately provided.

The present invention has been described in terms of exemplary embodiments. The invention, however, is not limited to the embodiments depicted and described and it is contemplated that other embodiments, which may be readily devised by persons of ordinary skill in the art based on the teaching set forth herein, are within the scope of the invention which is defined by the appended claims.

What is claimed is:

1. A method for increasing the concentration of a gas in the blood, comprising:
   withdrawing blood from a subject;
   directing blood flow through a mixing passage;
   introducing a gas-supersaturated fluid into the blood within said passage in axial alignment with said flow while minimizing bubble formation; and
   returning the blood to the subject.

2. The method of claim 1, wherein bubble formation is eliminated during and subsequent to gas-supersaturated fluid introduction.

3. The method of claim 1, further comprising the step of:
   pumping blood through said circuit at a rate of between about 25 ml/min and about 8000 ml/min.

4. The method of claim 1, wherein the gas-supersaturated fluid is an oxygen-supersaturated fluid.

5. The method of claim 1, wherein the gas-supersaturated fluid is introduced proximate to the center of the mixing passage.

6. The method of claim 1, wherein the site comprises the interior lumen of a tube.

7. The method of claim 1, further comprising the step of:
pumping blood through the circuit at a rate of between about 25 ml/min and about 200 ml/min.

8. The method of claim 1, further comprising the step of:
pumping blood through the circuit at a rate of about 100 ml/min.

9. A method for increasing the concentration of a gas in the blood, comprising:
withdrawing blood from a subject;
directing blood flow through a mixing passage defined by a passageway inner wall;
introducing a gas-supersaturated fluid into the blood along the passageway inner wall at a predetermined angle to the blood flow while minimizing bubble formation; and
returning the blood to the subject.

10. The method of claim 9, wherein said predetermined angle is selected to minimize turbulence in the blood flow due to fluid introduction at prevailing flow conditions.

11. The method of claim 9, wherein said predetermined angle is approximately forty-five degrees.

12. A method for increasing the concentration of a gas in the blood, comprising
withdrawing blood from a subject into an extracorporeal blood circulation circuit;
introducing a gas-supersaturated fluid into the blood at a site in said circuit while minimizing bubble formation;
reducing blood velocity at the site where the gas-supersaturated fluid is introduced; and
returning the blood to the subject.

13. The method of claim 12, further comprising increasing blood velocity subsequent to fluid introduction.

14. A method for increasing the concentration of a gas in the blood, comprising:
withdrawing blood from a subject into an extracorporeal blood circulation circuit;
introducing a gas-supersaturated fluid into the blood at a site in said circuit while minimizing bubble formation;
accumulating a volume of blood upstream of the fluid introduction site to help reduce flow variations at the fluid introduction site; and
returning the blood to the subject.

15. The method of claim 14, further comprising introducing compressed gas into a space above said accumulated blood volume.

16. The method of claim 14, wherein the volume of blood is accumulated to help dampen the pulsatility of the blood flow at the fluid introduction site.

17. A method for increasing the concentration of a gas in the blood, comprising:
withdrawing blood from a subject into an extracorporeal blood circulation circuit;
introducing a gas-supersaturated fluid into the blood at a site in said circuit while minimizing bubble formation;
filtering at least a portion of the fluid from the blood; and
returning the blood to the subject.

18. A method for increasing the concentration of a gas in the blood, comprising:
placing a sheath within a blood vessel in a patient and connecting the sheath to an extracorporeal blood circulation circuit input;
placing a catheter introducer into a different blood vessel or a different site of the same blood vessel of the patient;
advancing an intravascular catheter through said introducer;
connecting a circuit output to said catheter;
withdrawing blood from a subject through the sheath into said circuit;
introducing a gas-supersaturated fluid into the blood at a site in said circuit while minimizing bubble formation; and
returning the blood to the subject through the catheter.

19. The method according to claim 18, further comprising the step of treating said circuit with a wetting agent prior to said withdrawing step, said agent selected from the group consisting of water, ethanol and a heparin solution.

20. The method of claim 18, further comprising the step of:
placing in said circuit a priming volume of blood of less than about 20 ml.

21. A method for increasing the concentration of a gas in blood, comprising the steps of:
withdrawing blood from a subject into a blood circulation circuit;
introducing a gas-supersaturated fluid into the blood at a site in the circuit, wherein the gas-supersaturated fluid contains an amount of the dissolved gas that would occupy a volume of between about 0.5 and about 3 times the volume of a solvent contained in the gas-supersaturated fluid, wherein the amount is normalized to standard temperature and pressure; and
returning the blood to the subject.

22. The method of claim 21, wherein the gas-supersaturated fluid is introduced into the blood via one or more capillary channels.

23. The method of claim 22, wherein the capillary channels are made of silica.

24. The method of claim 21, wherein the subject is a human patient.

25. The method of claim 21, wherein the returning step comprises intravascular delivery of oxygenated blood.

26. The method of claim 21, wherein the oxygenated blood has a $pO_2$ greater than about 1000 mm Hg.

* * * * *